United States Patent [19]
Barta et al.

[11] Patent Number: 5,464,396
[45] Date of Patent: Nov. 7, 1995

[54] SYRINGE ASSEMBLY FOR THE STORAGE AND APPLICATION OF A BIOLOGICAL MULTI-COMPONENT MATERIAL

[75] Inventors: Helmut Barta; Helmut Eder; Manfred Granser; Georg Habison, all of Vienna; Edith Hantak, Seebarn; Franz Moser, Deutsch Wagram; Peter Pfaffenbichler, Podersdorf, all of Austria

[73] Assignee: Immuno AG, Vienna, Austria

[21] Appl. No.: 310,404

[22] Filed: Sep. 22, 1994

[30] Foreign Application Priority Data

Oct. 18, 1993 [AT] Austria .................................. 2085/93

[51] Int. Cl.⁶ ............................................... A61M 5/00
[52] U.S. Cl. ........................................... 604/191; 604/218
[58] Field of Search ............................ 604/191, 82, 187, 604/218, 310, 311

[56] References Cited

U.S. PATENT DOCUMENTS

| | | | |
|---|---|---|---|
| 2,112,160 | 3/1938 | Johnson | 128/234 |
| 3,223,083 | 12/1965 | Cobey | 128/92 |
| 3,552,394 | 1/1971 | Horn | 128/218 |
| 3,828,980 | 8/1974 | Creighton et al. | 222/137 |
| 4,040,420 | 8/1977 | Speer | 128/218 |
| 4,260,077 | 4/1981 | Schroeder | 222/137 |
| 4,359,049 | 11/1982 | Redl et al. | 128/218 |
| 4,631,055 | 12/1986 | Redl et al. | 604/82 |
| 4,735,616 | 4/1988 | Eibl et al. | 604/191 |
| 4,902,281 | 2/1990 | Avoy | 604/191 |
| 5,116,315 | 5/1992 | Capozzi et al. | 604/82 |
| 5,147,323 | 9/1992 | Haber et al. | 604/191 |
| 5,368,563 | 11/1994 | Lonneman et al. | 604/191 X |

FOREIGN PATENT DOCUMENTS

| | | |
|---|---|---|
| 2661097 | 10/1991 | France . |
| 2668060 | 4/1992 | France . |

*Primary Examiner*—John D. Yasko
*Attorney, Agent, or Firm*—Foley & Lardner

[57] ABSTRACT

There is disclosed a syringe assembly for the storage and application of a biological multi-component material. Its assembly parts are a syringe device including several parallel syringe bodies interconnected by a connection part, which syringe bodies are filled with the individual components of the multi-component material, include coni and are closed by pistons; an actuation device for this syringe device, which includes piston rods associated with the pistons and a common grip element; and a dispensing element to be attached to the coni of the syringe bodies. The filled syringe bodies, which are closed by separate piston plugs, constitute a one-piece syringe unit with the connection part. The connection part leaves a recess between the syringe bodies on one of the ends of the syringe unit for receiving a protection means shielding off the other syringe body/ies when filling the syringe bodies. The grip element is connected in one piece with the piston rods, thereby forming a one-piece piston rod unit separate from the syringe unit including the piston plugs.

38 Claims, 7 Drawing Sheets

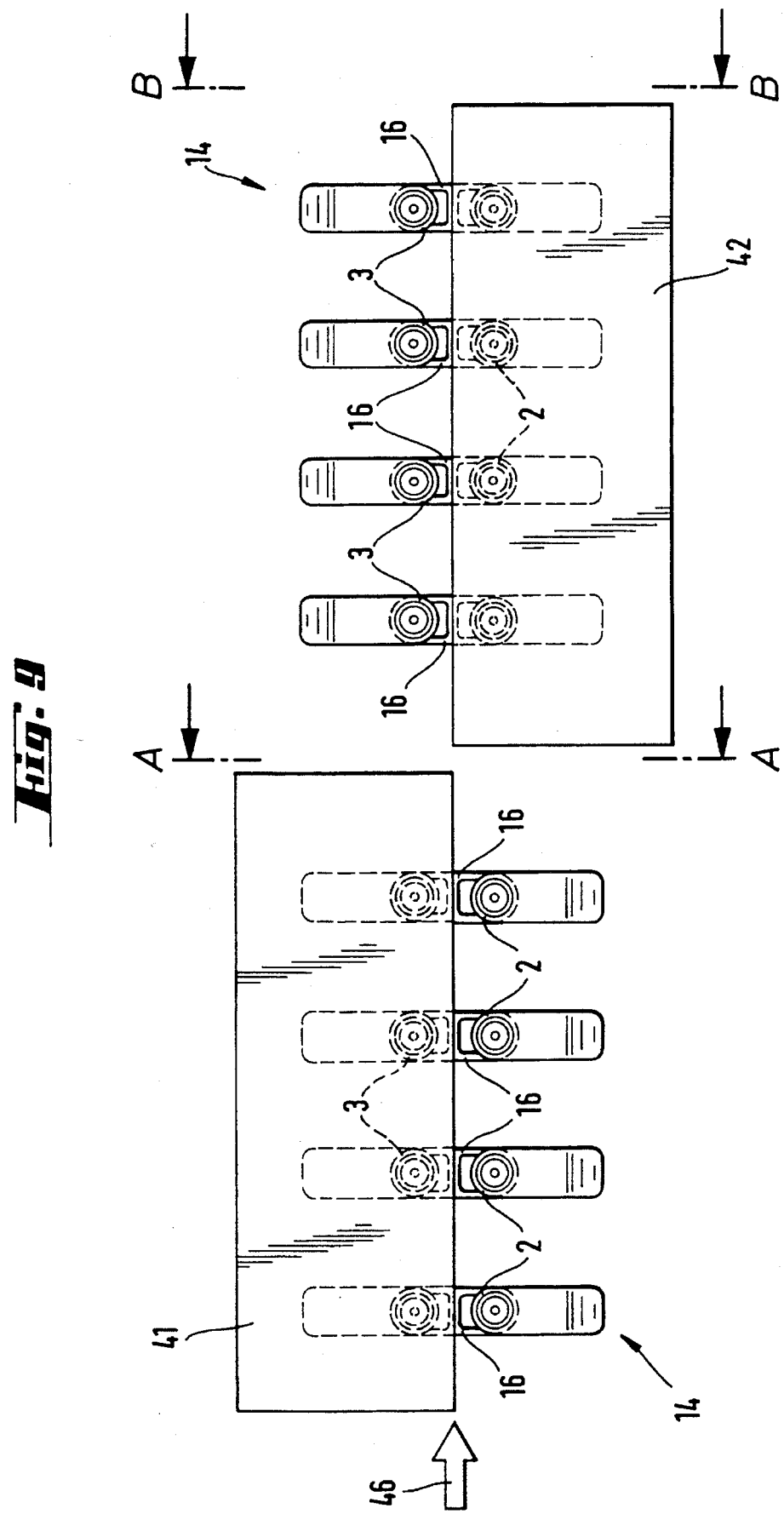

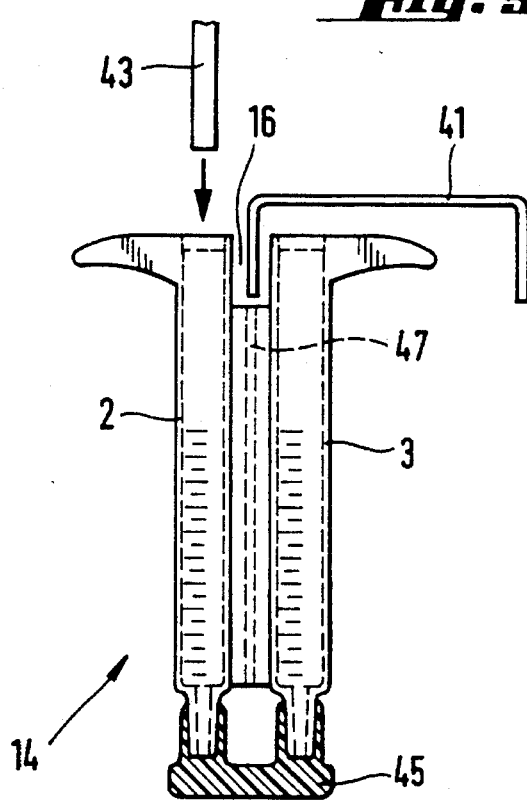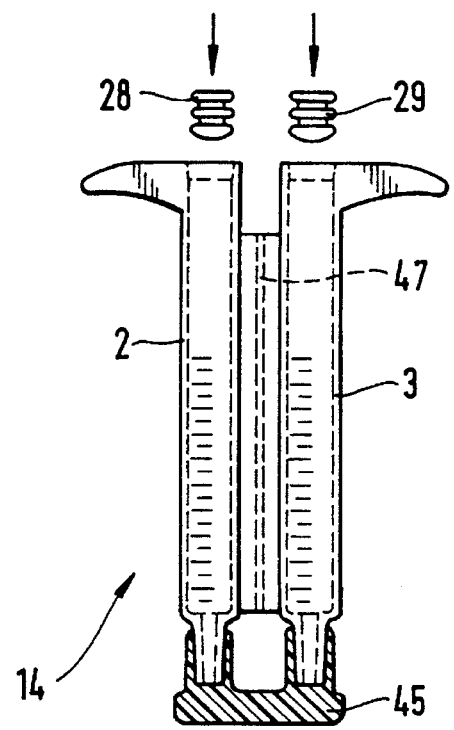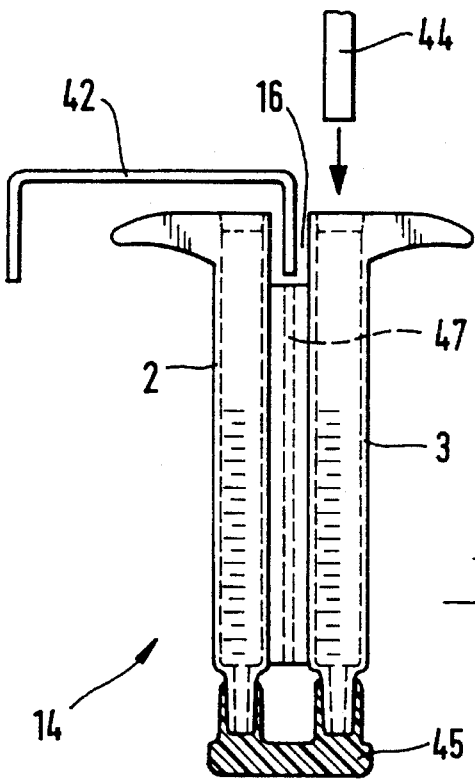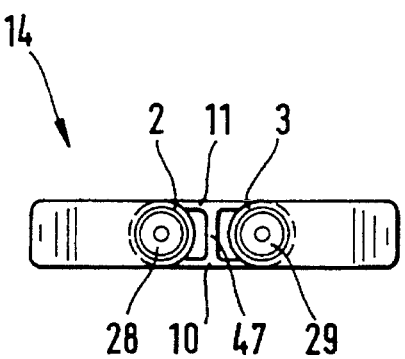

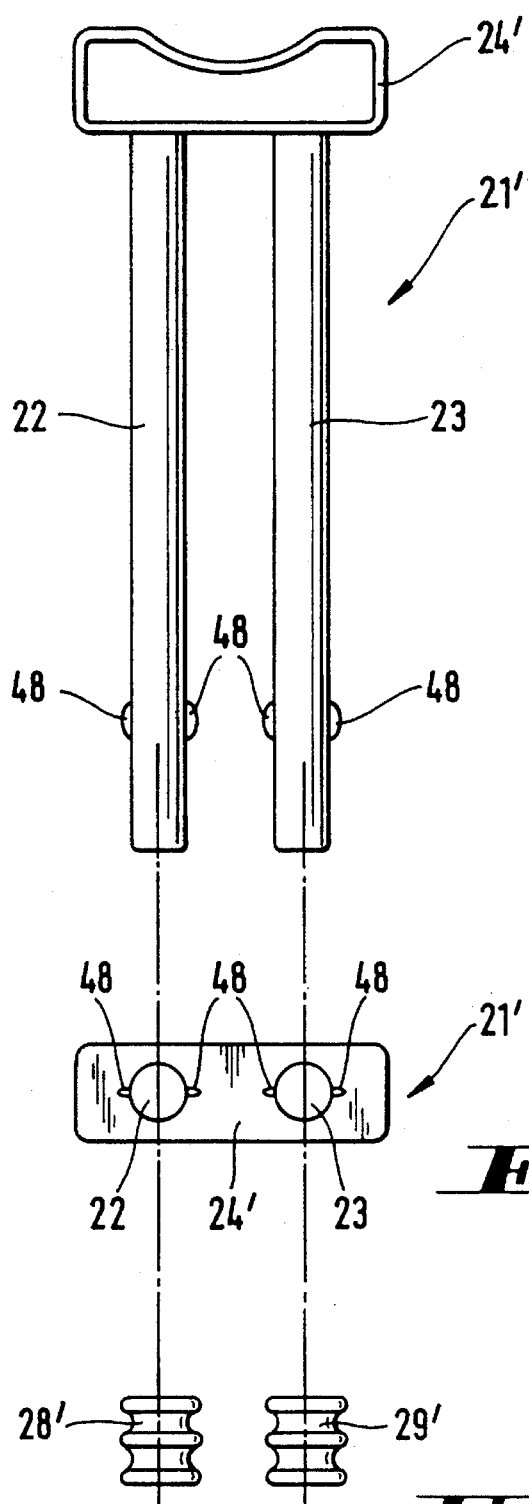
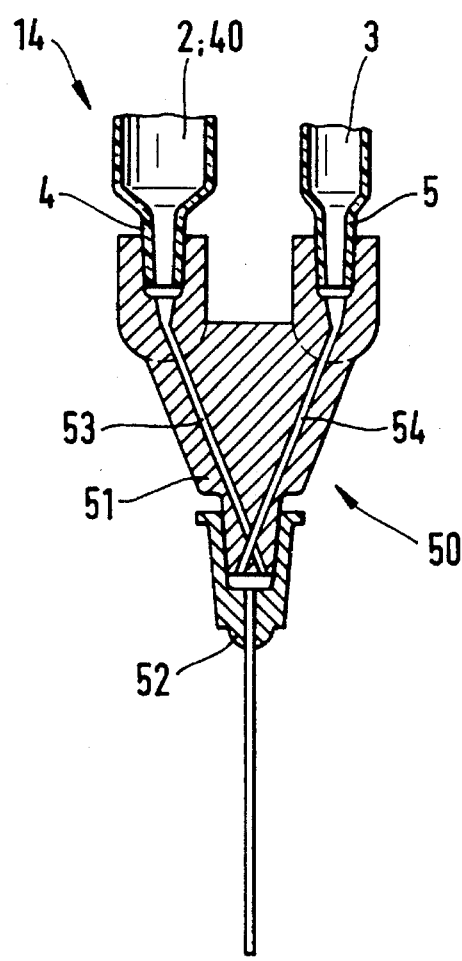

SYRINGE ASSEMBLY FOR THE STORAGE AND APPLICATION OF A BIOLOGICAL MULTI-COMPONENT MATERIAL

The invention relates to a syringe assembly adapted for the storage and application of a biological multi-component material, preferably a tissue adhesive based on human or animal proteins for seamlessly or seam-supportingly connecting human or animal tissue or organ parts, for sealing wounds, stopping bleedings and the like, which comprises as assembly parts a syringe device including several parallel syringe bodies interconnected by a connection part, which syringe bodies are filled with the individual components of the multi-component material, include coni and are closed by pistons, an actuation means for the syringe device, including piston rods associated with the pistons and a common grip element, and a dispensing element to be attached to the coni of the syringe bodies.

The invention, furthermore, relates to a syringe device adapted for the storage and application of a biological multi-component material, comprising several parallel syringe bodies interconnected by a connection part and preferably made of synthetic material, for the various components of the multi-component material, the syringe bodies forming a one-piece syringe unit with the connection part.

Moreover, the invention similarly relates to an actuation device for a syringe device adapted for the storage and application of a multi-component material, comprising several interconnected parallel syringe bodies closed by pistons, said actuation device comprising piston rods associated with the pistons of the syringe bodies, and comprising a common grip element.

Also, the invention is related to a method of producing a filled sterile syringe device.

Application assemblies of the general type as indicated above, comprising a syringe device, a common actuation means for the pistons of all of the syringe bodies, and a dispensing element, for instance, in the form of a spraying head or a connection head to which a spraying catheter is connected, or a mixing cannula, are known, for instance, from EP-A-37,393 (and its corresponding U.S. Pat. No. 4,359,049), EP-A-156,098 (and its corresponding U.S. Pat. No. 4,631,055) as well as EP-A-210,160 (and its corresponding U.S. Pat. No. 4,735,616). Similar application assemblies are disclosed in U.S. Pat. No. 5 116,315 and in FR-A-2,661,097. Such assemblies, in particular, are used to apply a tissue adhesive which is solidified in situ when united with blood coagulation promoting coagulation enzymes, a factor XIII and fibrinogen containing protein solution (tissue adhesive) on the one hand, and a thrombin containing solution, on the other hand, being used as components. In case of use, these components are applied on the desired site, e.g., on a wound to be treated or protected, through the dispensing element connected with the syringe bodies of the syringe device—for instance, the connection head with the mixing cannula or the spraying head—by attachment to their syringe coni.

With the known assemblies, a generally trough- or sleeve-shaped retaining means including appropriate troughs or sleeves for receiving the syringe bodies is provided to connect the syringe bodies, which retaining means, in addition, is provided with finger grips laterally projecting in opposite directions. The syringe bodies are inserted in these retaining means, wherein for instance, elastically yielding snap-in projections hold fast the syringe bodies. To actuate the pistons of the syringe bodies, the piston rods that are firmly connected with the pistons, furthermore, are connected with a common grip element, and, for stabilizing and improving the guidance of the piston rods when actuating the syringe device, it has also been proposed to connect a guide rod with the common grip element; such guide rod extends through a guide bore within the retaining means.

By such a design, a substantial progress in terms of simple mounting and greater safety in manipulation has been achieved as compared to earlier designs, such as according to U.S. Pat. No. 3,223,083 or U.S. Pat. No. 2,112,160, since, on the one hand, the syringe bodies may, for instance, be snapped in the retaining means and, on the other hand, the piston rods are interconnected for jointly operating the pistons and, moreover, are guided by the guide rod when moved such that a uniform actuation of the pistons of all of the syringe bodies will be ensured. By contrast, with the arrangement according to U.S. Pat. No. 2,112,160, the syringe bodies, which directly contact each other longitudinally, are connected in a complex manner by a cement mass as well as by wire loops and rubber bands. With the arrangement according to U.S. Pat. No. 3,223,083, the syringe bodies are connected with one another by a clamp enclosing them on a central point, wherein the syringe bodies do not assume a stable position relative to one another. Moreover, the two piston rods must be pushed forward by the user simultaneously and as uniformly as possible, which requires great skill.

It has now been shown that the syringe assemblies of the type in question, e.g., according to EP-A-37,393 or EP-A-156,098, still are disadvantageous inasmuch as the mounting of the syringe bodies in the retaining means as well as the connection of the piston rods via the common grip element practically cannot be realized automatically but only manually, a sterile operation, thus, being rendered difficult and additional sterilization treatments being necessary. Sterile filling is feasible with great expenditures only.

It is now desirable to render feasible in a simple manner the sterile or aseptic treatment of the assembly parts and, in particular, of the syringe device during the entire manufacturing, filling and packaging process until taking into use. Such aseptic or sterile manufacture, filling and packaging is of very special importance, in particular, with respect to the special components for the preferred use of the application assembly, i.e., the application of a tissue adhesive.

Moreover, relatively great manufacturing expenditures are required with the known application assemblies inasmuch as, in addition to the syringe bodies for the syringe device and the pistons with the piston rods and the actuation means, several separate structural elements, i.e., the retaining means on the one hand, and the common grip element together with the guide rod, on the other hand, must be produced, these structural elements subsequently having to be connected—manually—with the corresponding elements.

On the other hand, double syringes have already been proposed (cf. U.S. Pat. No. 3,828,980 and U.S. Pat. No. 4,040,420) in which the syringe cylinders longitudinally are directly molded to one another so as to provide for simpler manufacture and manipulation as compared to the abovementioned syringe assemblies. However, they involve the disadvantage that filling of the syringe cylinders with the different components—which must not get into contact with one another prior to application—is particularly difficult without mutual contamination because of the immediate vicinity of the syringe cylinders. Moreover, the simultaneous actuation of the two pistons also is difficult.

A different type of double syringe having two separate injection needles, finally, is known from U.S. Pat. No.

3,552,394, wherein the two syringe bodies are united by a connection part which is stepped in its thickness to a one-piece syringe unit into which the syringe chambers are bored. It is sought to reduce the pain felt by a patient by arranging the two injection needles relatively closely adjacent each other such that only a single pricking pain will be felt when inserting both needles. Also there, it is disadvantageous, i.a., that the separate filling of the two syringe ampoules with different substances is critical.

Therefore, it is an object of the invention to eliminate such difficulty and to provide a syringe assembly, a syringe device as well as an actuation means, of the initially defined kind, wherein, on the one hand, aseptic treatment is ensured during the entire manufacture, filling and packaging of the syringe device and the independent subsequent sterilization of the remaining assembly parts is feasible and, on the other hand, a simple construction can be realized without requiring special additional structural elements, and wherein, moreover, the simple and safe operation of the pistons of all of the syringe bodies is to be guaranteed. In addition, a method is to be provided, which safeguards sterility in an economic manner during manufacture and filling of the syringe device.

The syringe assembly according to the invention, of the initially defined kind is characterized in that the filled syringe bodies, which are closed by separate piston plugs, constitute a one-piece syringe unit together with the connection part, and that, furthermore, the connection part leaves a recess between the syringe bodies on one of the ends of the syringe unit, preferably on the end opposite the coni, for receiving a protection means shielding off the other syringe body/ies when filling the syringe bodies, and in that the grip element is connected in one piece with the piston rods, thereby forming a one-piece piston rod unit separate from the syringe unit including the piston plugs.

Similarly, the syringe device according to the invention, of the initially defined kind is characterized in that the connection part leaves a recess between the syringe bodies on one of the ends of the syringe unit, preferably on the end opposite the coni, for receiving a protection means shielding off the other syringe body/ies when filling the syringe bodies.

Furthermore, the actuation device according to the invention, of the initially defined kind is characterized in that the grip element is connected in one piece with the piston rods, thus forming a onepiece piston rod unit.

Finally, the method according to the invention is characterized in that the syringe bodies of a sterile syringe unit sterilely produced in one piece and kept sterile or sterilized after production, the one syringe body ends of which have been sealed, after introduction of a protection means into the recess between the (respective) syringe bodies on their other ends for shielding the respective other syringe body/ies, are automatically filled with the components of the biological multi-component material in a filling station under sterile conditions and subsequently are closed by sterile piston plugs.

By the above-described measures, the aims set out above are achieved in an advantageous manner. The syringe device is formed by a compact stable syringe unit associated with a likewise compact stable piston rod unit. Both units can be produced, i.e., can be molded in one piece, completely automatically without any problem, which is of particular relevance primarily in respect of the sterility and "free-of-particle feature" sought with the syringe assembly. As regards the piston rod unit, subsequent sterilization in the already packed state is possible without any problems similar as with the dispensing element, i.e., it is not necessary to produce the piston rod unit, or insert it into the syringe unit, in a sterile area. The piston rod unit also may be packed together with the dispensing element (e.g., a connection piece including separate channels for conveying the individual components, if desired, including a mixing cannula) in a common package and subjected to a sterilizing treatment afterwards.

Thus, it is possible in an advantageous manner for the syringe units to let all procedures from manufacture, preferably by injection molding, via possible packaging and unpackaging of the syringe unit, individually detaching the syringe units for automatical filling of the syringe bodies, until closure of the same by the piston plugs and packaging, run aseptically without requiring any manual manipulations. This is of very particular advantage primarily with regard to the preferably used substances to be applied, i.e. protein solutions, etc. The syringe device according to the invention, still empty or already filled, thus is characterized by being sterile at any stage.

In automatical filling of the syringe bodies, a protection means, for instance, in the form of a cover angle is provided to prevent mutual contamination with the components or reaction liquids, which cover angle projects into the receiving recess between the (respective) syringe bodies, thereby separating and shielding off the remaining syringe body/ies from the as-filled syringe body. In principle, it is also conceivable to insert into the recess a protective sheet or the like protection means between the syringe bodies in a manner that the syringe bodies on either side of this protection means are being filled simultaneously, wherein mutual contamination is effectively prevented by this protection means also in that case. Thus, the feature of the recess between the syringe bodies for receiving the protection means to be inserted during filling substantially contributes to rendering possible the sterile automatical filling while guaranteeing the simple one-piece compact structure of the syringe unit, nevertheless.

Suitably, the syringe unit, the piston rod unit and/or the dispensing element may comprise X-ray absorbing material, at least in regions, e.g., in the form of a strip; a metal strip may, for instance, be molded in. In this manner, subsequent detection is possible by means of an X-ray device.

Furthermore, it is advantageous, primarily for safety reasons, e.g., in order to prevent a physician from erroneously retracting the piston plugs during use, if the piston plugs are displaceable within the syringe bodies by means of the piston rod unit only in the direction of the coni. This may be accomplished, for instance, by rendering the frictionally engaged seat of the piston plugs in the syringe bodies more firmly than, for instance, a snap-in seat of the piston rods in rear openings of the piston plugs in case of tensional stress.

However, it is particularly suitable if the piston rods simply abut on the rear side of the piston plugs, wherein a slight frictionally engaged support may be provided for the piston rods in the syringe bodies, for instance, by projecting wings, in order to prevent them from falling out when in use. The separate piston plugs can be made entirely of silicone material, which is advantageous with regard to the desired sliding properties over long periods of time (e.g., 2 years) and to the required purity (wherein, e.g., no lubricant must be used).

In a preferred embodiment, piston plugs are used which are comprised of full material and are ball-shaped. Such piston plugs possess just one sealing lip, which facilitates the advance of the piston plug in the direction of the coni. A further advantage of this embodiment consists in that the piston plugs can be inserted in a simple manner after the syringe bodies have been filled, because no particular orientation of the piston plugs need be taken into account.

When using piston rods with appropriate recesses, simple displacement of these ball-shaped piston plugs while maintaining tightness is possible only in the direction of the coni by pressing on the piston rods. In this case, the coni are configured correspondingly concave in order to ensure the complete emptying of the syringe bodies.

In this connection, it should be noted that from U.S. Pat. No. 5,147,323 an ampoule unit is known, which comprises several ampoules arranged one beside the other in a box-shaped container, which ampoules are rearwardly closed by simple loose piston plugs; according to the position of a slide cover closing the container and including an opening for introducing a piston rod, the piston plug can be pushed forward in one of the ampoules in order to cause a dose of insulin to be dispensed via a needle capable of being pushed out. This known ampoule unit, as a whole, is extremely complex and expensive and is hardly suitable for the application of a tissue adhesive.

To obtain a particularly high strength of the syringe unit against torsion or breaking, it has proved to be particularly advantageous if, as connection element, at least two parallel plate-shaped connection webs extend between the syringe bodies connected to one piece by the same. Therein, it is, furthermore, beneficial if each connection web tangentially joins the respective syringe body. In general, the syringe unit may be designed flat and plate-shaped so as to be readily manipulated, having a thickness corresponding to the thickness or external diameter of the syringe body. Such a flat compact plate-shaped syringe unit, of course, is suitable for any kind of manipulation in addition to the fact that such a syringe unit exhibits a particularly high resistance to breaking. Moreover, the connection webs can be manufactured with thicknesses comparable to the wall thicknesses of the syringe bodies without any problem such that no difficulties occur even during cooling when produced by molding or the like.

From EP-A-210,160 (and the corresponding U.S. Pat. No. 4,735,616) it is already known to provide the syringe bodies with different cross sections at equal piston stroke lengths in order thereby to render feasible varying mixing ratios of the protein solution and of the thrombin solution deviating from the ratio 1:1, in the case of application of a tissue adhesive. With the known arrangement, appropriately dimensioned circularcylindrical syringe bodies are snapped in the appropriately dimensioned troughs of the retaining means. With the last-mentioned embodiment of the arrangement according to the invention, varying mixing or dissolution ratios are likewise feasible despite the flat plate-shaped configuration of the whole syringe unit. An advantageous embodiment of the device according to the invention, therefore, is characterized in that, when providing syringe bodies having different cross sectional areas and constant piston stroke lengths, the cross sectional area of at least one of the syringe bodies is oval, its dimension transverse to the thickness direction of the plate-shaped syringe unit being different from that of the cross sectional area of the other syringe body/ies.

A configuration that is particularly simple to manufacture, on the other hand, is rendered feasible if a connection web extending in a plate-shaped manner along a central plane defined by the longitudinal axes of the syringe bodies and centrally joining the respective syringe body is provided as said connection element.

In order to effectively prevent mutual contamination on the one hand and not to affect the strength of the connections of the syringe bodies by means of the connection web(s) by too deep a reception recess, it has been proved to be a particularly advantageous compromise with current syringe dimensions if the (respective) connection element terminates at a distance of at least 2 mm, preferably at a distance of 5 mm to 15 mm, in particular of about 10 mm, from an end of the syringe unit so as to leave the reception recess free.

As already mentioned, the known syringe devices of the type in question comprise finger grips on the trough-shaped retaining means, which laterally project from the retaining means relative to the syringe bodies in opposite directions. Finger grips may, of course, also be provided with the syringe device according to the invention, wherein it is suitable to simply mold the finger grips directly to the rear ends of the syringe bodies. The finger grips may have a width comparable to the external diameter of the syringe bodies so as to lie within the thickness dimension of the syringe unit in case of the particularly preferred flat plate-shaped configuration of the syringe unit.

It would be conceivable to firmly connect in one piece the syringe bodies and the connection web(s), for instance by welding, such as ultrasonic welding. However, with regard to a simple manufacture as well as a uniform compact arrangement, it is particularly preferred if the syringe unit is a one-piece polypropylene injection-molded part. Polypropylene is particularly suitable for the production of the syringe bodies, because it does not have what is called a "release" property, i.e., no components, such as plasticizers, etc., migrate from the material into the content of the syringe, i.e., into the respective product received by the syringe body.

Also, it is advantageous if the, or at least one, connection element comprises at least one inscription area. On this inscription area, an inscription, for instance, relating to the content of the syringe bodies, the type of application, etc., may be made prior or after filling of the syringe bodies. In this connection, it is conceivable for an inscription to directly make an impression on the field of inscription or to apply, e.g., glue on, an inscription label or the like. Also, it would be possible to apply an inscription by embossing when molding the syringe unit, wherein such relief-type embossed structure also would have a certain effect of reinforcement for the connection web. However, it is, of course, also possible to mold reinforcement ribs or the like to the connection webs independently thereof.

With the actuation means according to the invention, it is, furthermore, particularly advantageous to provide a reinforcement web joining the grip element, which extends between the piston rods and is firmly connected therewith, for additionally reinforcing the piston rod unit and for increasing the strength of the connection between the piston rods.

Also here, it is again preferred if the piston rod unit is a one-piece injection-molded part.

The actuation device or piston rod unit is inserted in the syringe device only at a later point of time after filling of the syringe bodies and closing of the same by inserting the piston plugs, in particular, only immediately before use. Thereby, the piston rod unit will not get into direct contact with the substances contained in the syringe bodies. Accordingly, the choice of material for the piston rod unit is not that critical, the material being choosable primarily with regard to the simple manufacture desired and the high strength of the piston rod unit sought. In this connection, it has been proved particularly advantageous to make the piston rod unit of an acrylonitrile-butadiene-styrene copolymer (ABS).

When producing the filled syringe device while maintaining sterility, it is also particularly advantageous if the syringe device is sterilely packed immediately upon filling with the components and closing by the piston plugs. Furthermore, it is beneficial if the corresponding syringe bodies of a plurality of syringe units arranged in a row each are sterilely filled simultaneously while introducing a common protection means (each) into the recesses of these syringe units.

In the following, the invention will be explained in more detail by way of particularly preferred exemplary embodiments illustrated in the drawing, to which it is, however, not limited. In the drawings.

FIGS. 9, 9A and 9B schematically illustrate the automatic filling of a syringe unit in a filling station with two components to be kept separate, FIG. 9 being a schematic top view on syringe units filled in a line, FIGS. 9A and 9B being schematic views along lines A—A and B—B, respectively, of FIG. 9;

FIG. 10 schematically illustrates the closing of a syringe unit by using pistons;

FIG. 11 is a top view on the closed syringe unit;

FIGS. 12 and 13 represent a further piston rod unit particularly preferred at present, in an elevational view and in a bottom view, respectively, FIG. 14 is a view of solid piston plugs for cooperation with the piston rod unit according to FIGS. 12 and 13; and FIG. 15 is a view of a dispensing element in the form of a plug-on head including a mixing cannula known per se, to complete the illustration of the syringe assembly parts.

Figure 1:
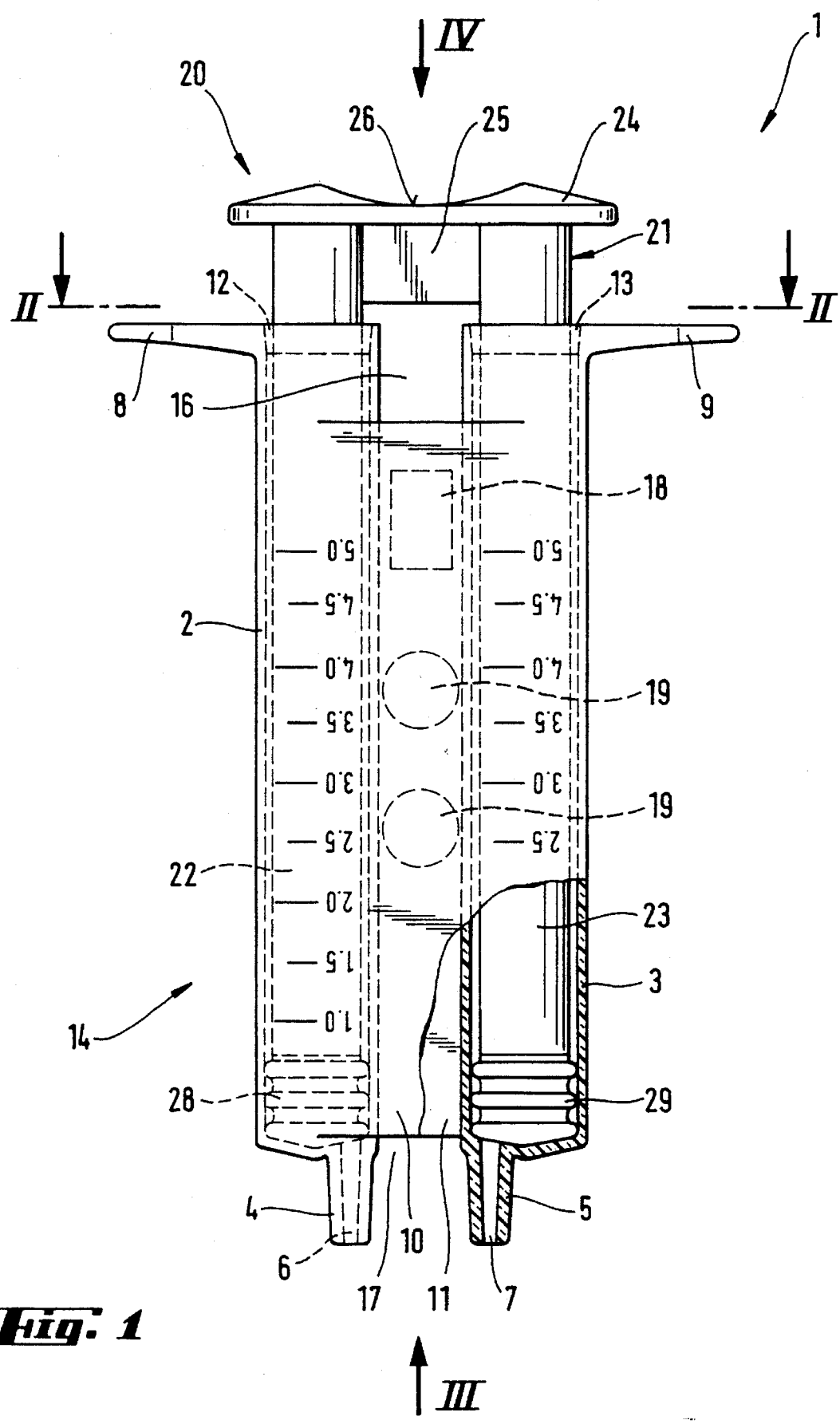
FIG. 1 is a schematic view of a syringe device for application of a tissue adhesive with a piston rod unit being inserted therein.

FIG. 1 depicts a syringe device generally denoted by 1 as part of a syringe assembly intended for the storage and application of a tissue adhesive based on human or animal proteins. The syringe device 1 includes two syringe bodies 2, 3, one of which serves to receive a thrombin containing solution and one of which serves to receive a factor XIII and fibrinogen containing solution. As is apparent from FIGS. 2 and 3, the syringe bodies 2, 3 have circular cross sections in the exemplary embodiment illustrated and, on their forward ends, each have a syringe conus 4 and 5, respectively, in a manner known per se, which may be closed in a conventional manner by a closure cap (not illustrated in FIG. 1, yet cf. cap 45 in FIGS. 9A, 9B and 10) until use. In use, a dispensing element, for instance, an attachment or collection head including a mixing cannula (cf. FIG. 15 to be explained), a connection piece including a cannula or a spraying head, is attached to the syringe coni 4, 5 as a further syringe assembly part as is known per se.

Figure 2:
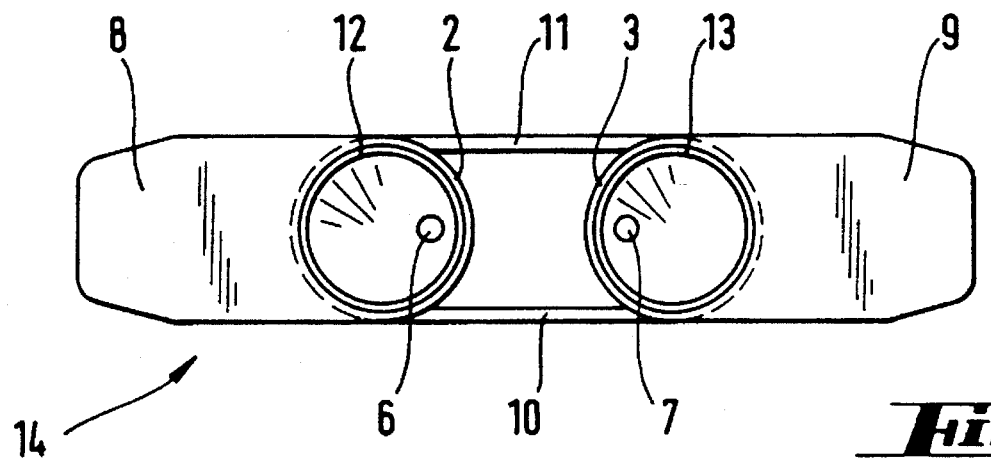
FIG. 2 is a top view on the syringe device along line II—II of FIG. 1, with the piston rod unit removed.

FIGS. 1 and 2, furthermore, show the bores 6, 7 provided in the syringe coni 4, 5.

To the rear ends of the syringe bodies 2, 3, finger grips 8, 9 are directly molded, said finger grips grips laterally projecting from the syringe bodies 2, 3 in opposite directions.

The syringe bodies 2, 3 are interconnected by a forward and a rear connection web 10, 11, respectively, (cf. also FIGS. 2 and 3) to a rigid, compact, flat, plate-shaped unit that cannot be disassembled. These connection webs 10, 11, by their external sides, tangentially join the external side of the cylindrical syringe bodies 2, 3, and extend almost over the total length of the syringe bodies 2, 3, yet each ending at a distance from the forward end (syringe conus end) and from the rear end (where the syringe bodies 2, 3 are provided with a chamfer 12, 13), respectively, such that both on the forward end and on the rear end of the syringe unit 14 formed by connecting the syringe bodies 2, 3, recesses 16 and 17, respectively, are left for introducing a protection means, for instance, in the form of an angled cover plate as will be explained later on with reference to FIGS. 9, 9A and 9B, during mechanical filling of the syringe bodies 2, 3.

The connection webs 10, 11 are formed in one piece with the syringe bodies 2, 3, in particular, are injection-molded, polypropylene being primarily preferred as a material for the one-piece syringe unit 14.

As is schematically illustrated in FIG. 1 by broken lines, one or more inscription areas 18, 19 may be provided on the connection webs 10, 11 for either directly making an impression thereon or attaching a printed label or the like thereto. Preferably, the total external side (front side) of the forward connection web 10 and the total external side (back side) of the rear connection web 11 are used as inscription areas.

Figure 4:
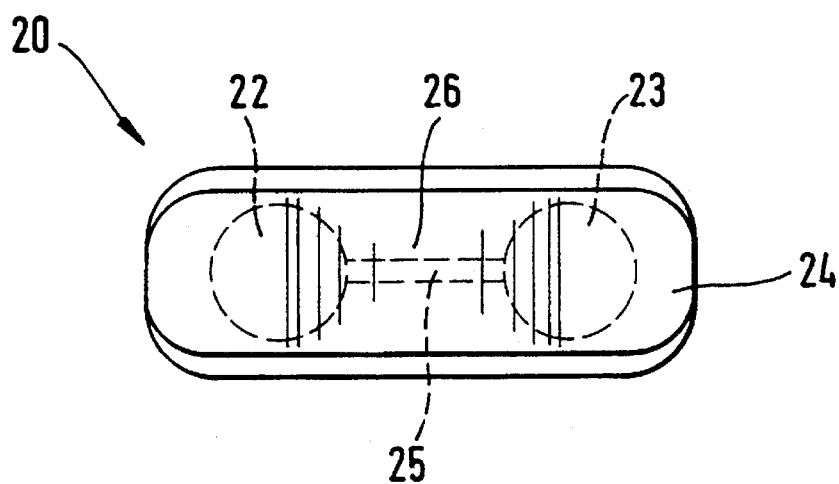
FIG. 4 is a top view on the piston rod unit of the syringe device of FIG. 1, according to arrow IV in FIG. 1.

The actuation device 20 associated with the syringe device 1 is comprised of a separate one-piece piston rod unit 21 including two piston rods 22, 23, which are connected on their rear ends, upper ends in FIG. 1, in one piece by a common grip element 24 on whose lower side a one-piece co-molded reinforcement web 25 joins, which connects the piston rods 22, 23, too. The grip element 24 is provided with a recessed grip 26 against which the thumb bears when operating the syringe device 1. The piston rods 22, 23, for instance, are of circular-cylindrical cross section, as is apparent, in particular, from FIG. 4, and may be full or hollow.

When using the syringe device 1, the forward ends of the piston rods 22, 23 of the actuation device 20 are engaged with the piston plugs 28, 29, respectively, which have already been inserted in the syringe bodies 2, 3 after filling for closing the same, as will be explained in more detail by way of FIGS. 9 to 11.

The piston rod unit 21, besides the syringe device 1, constitutes another part of the syringe assembly without the piston plugs 28, 29 which are located in the filled syringe device 1, and, preferably, it is also produced as an injection-molded part, for instance, of ABS.

The piston plugs 28, 29, for instance, may be configured for a snap-in or catch connection with the forward ends of the piston rods 22, 23, as will be explained in even more detail by way of FIG. 7, or preferably may simply consist of full material, on which the piston rods 22, 23 come to abut when in use, as will be explained later on by way of FIGS. 12 to 14.

The embodiment according to FIGS. 5 to 8 largely corresponds to that represented in FIGS. 1 to 4 so that the following description of this second embodiment primarily is limited to the differences between the two embodiments.

Otherwise, the same reference numerals are used in FIGS. 5 to 8 for the individual elements as have been used for the corresponding elements of the embodiment according to FIGS. 1 to 4. In the embodiment according to FIGS. 5 to 8, piston rods 22', 23' having star-shaped cross sections are provided in the piston rod unit 21 to ensure the uniform cooling and solidification of the material in injection molding on account of the material thicknesses comparable throughout. Otherwise, the piston rod unit 21 according to FIGS. 5 to 8 corresponds to that of FIGS. 1 and 4, a grip element 24 designed in one piece with the piston rods 22', 23' as well as a reinforcement web 25, in particular, again being provided. In respect of the remaining description of the piston rod unit 21, it may, therefore, be referred to the afore-described explanations.

Figure 7:
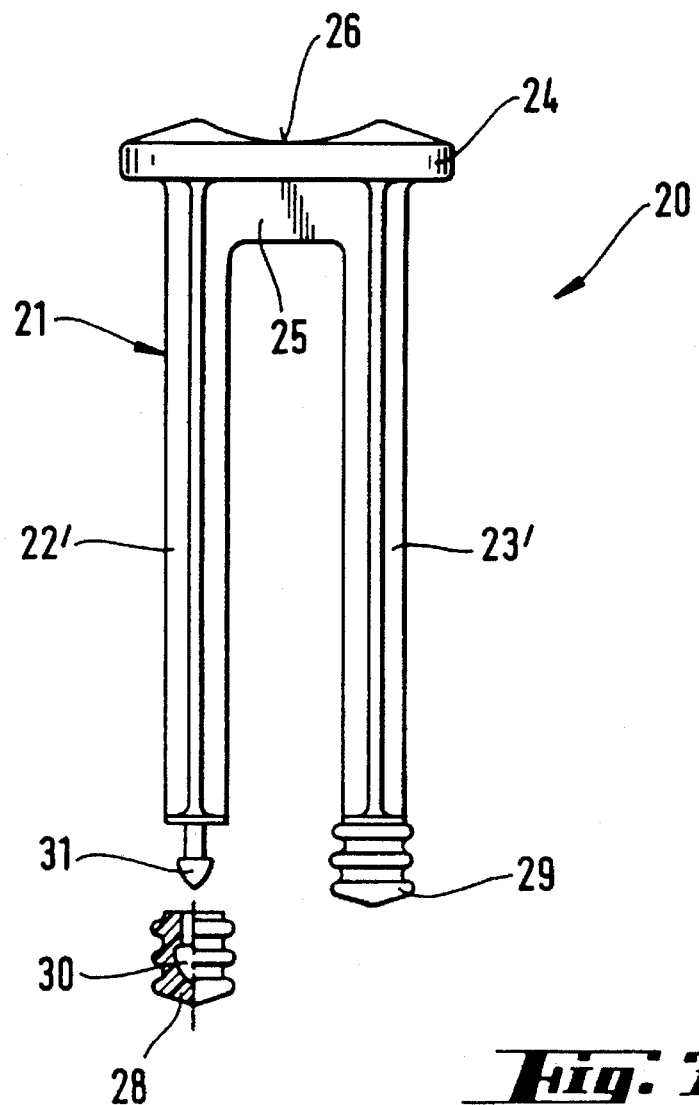
FIG. 7 is a view of the actuation means or piston rod unit, one of the pistons being represented in an explosive and partially cut away view and the other piston being represented in a position snapped onto the piston rod.

From FIG. 7 it is also apparent that the piston plugs, e.g., 28, may include an undercut bore 30, which cooperates with a latch-in head 31 provided on the forward ends of the piston rods, e.g., 22', and widened in a barb-shaped manner when assembled with the same such that the latch-in head 31 will snap in the bore 30 when pressing the piston rods 22, 23 or 22', 23', respectively, on the piston plugs 28 and 29.

Figure 5:
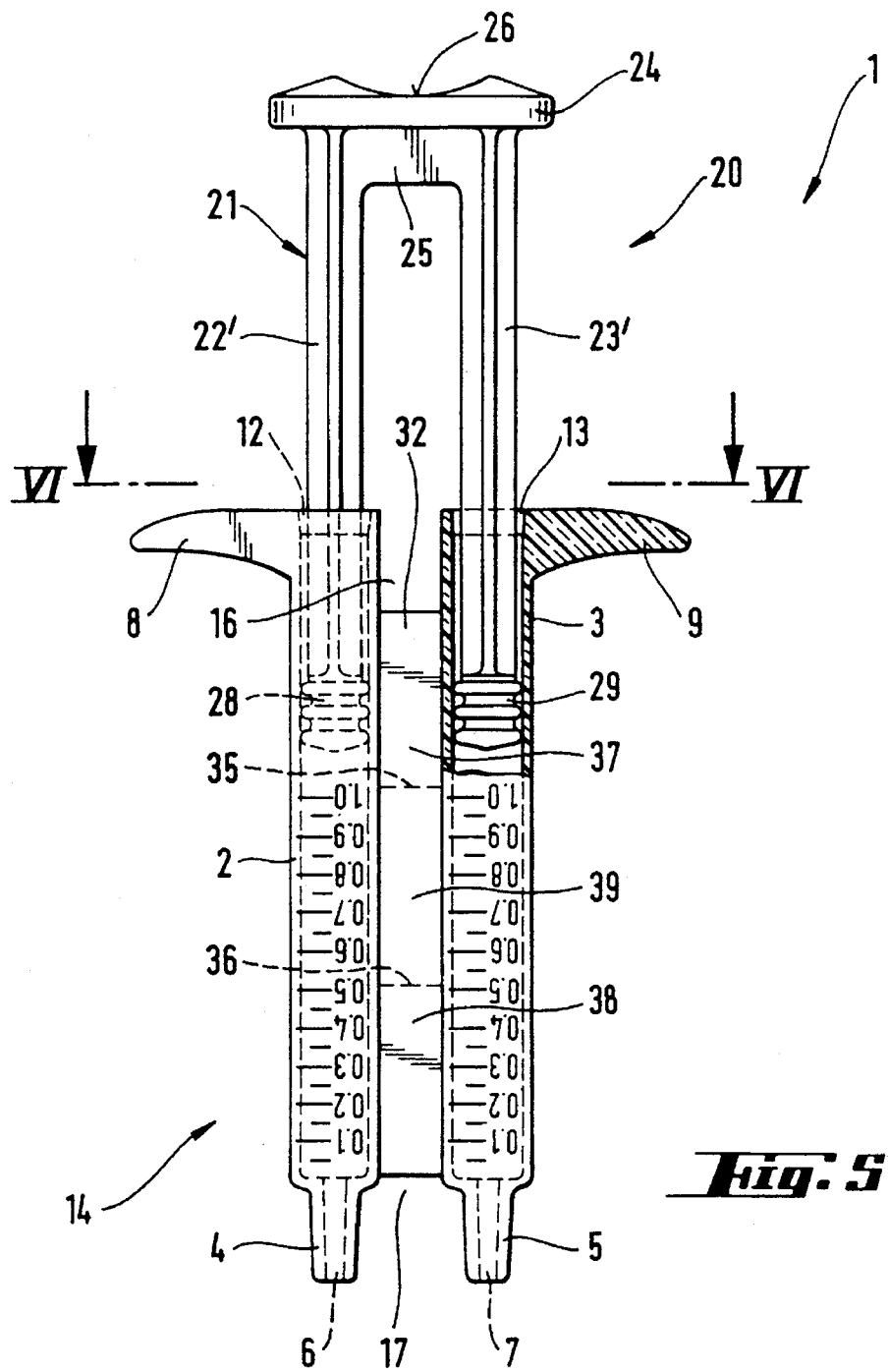
FIG. 5 represents another embodiment of a syringe device in schematic illustration, with the piston rod unit inserted therein.
Figure 6:
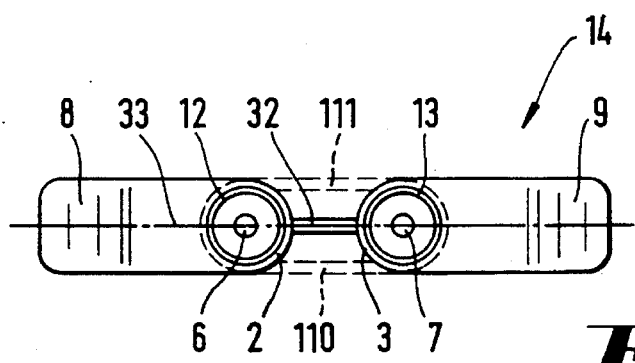
FIG. 6 is a top view on the syringe device along line VI—VI in FIG. 5, with the piston rod unit removed.

Contrary to the syringe unit according to FIGS. 1 to 4, a single central connection web 32 is provided with the syringe unit 14 according to FIGS. 5 and 6, which, in general, extends through a central plane containing the longitudinal axes of the syringe bodies 2, 3 and represented by a dot-and-dash line 33 in FIG. 6. In addition to, or thereinstead, connection webs 110, 111 tangentially joining the syringe bodies 2, 3 may be provided—similar to the connection webs 10, 11 in the embodiment according to FIGS. 1 to 4—as is illustrated in FIG. 6 by broken lines.

Also with the syringe unit 14 according to FIG. 5, the central connection web 32 again ends at a distance from the forward end (syringe coni 4 and 5) and from the rear end of the syringe unit 14, which distance preferably amounts to at least 2 mm, e.g., approximately 5 mm to 15 mm, in particular 10 mm; thus, reception recesses 16, 17 for the introduction of a protection means between the syringe bodies 2, 3 during filling of the same are again provided.

The connection web 32 between the syringe bodies 2, 3 also may be divided into various inscription areas as is indicated in FIG. 5 by broken lines 35, 36 such that, for instance, an upper inscription area 37 and a lower inscription area 38 are provided having a free area 39 therebetween.

Figure 3:
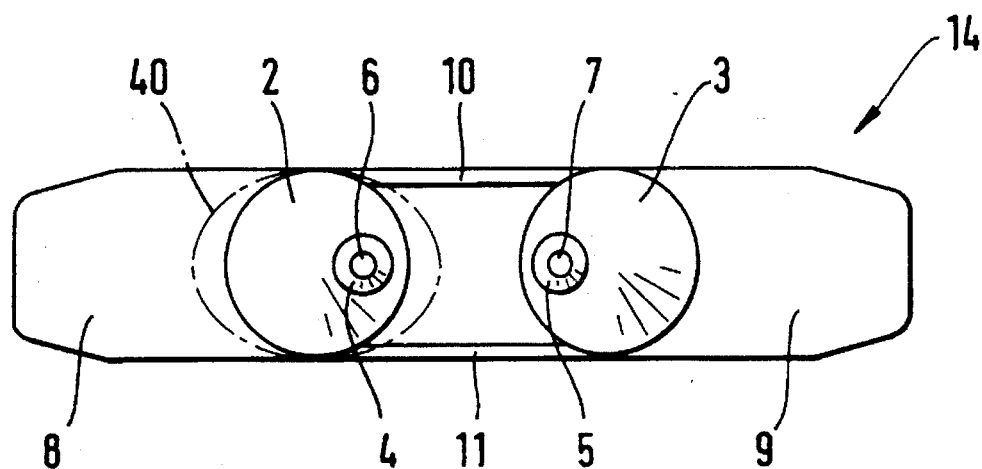
FIG. 3 is a bottom view of the syringe device of FIG. 1 according to arrow III in FIG. 1.

If a mixing ratio deviating from a 1:1 ratio is desired on account of a predetermined particularly desired solution concentration of the reaction liquid to be applied, this can advantageously be achieved with the instant application arrangement 1, in particular, in the flat plate-shaped configuration according to FIGS. 1 to 4 where a constant transverse dimension would be desired over the total width of the arrangement, in that one of the syringe bodies, e.g. 2, is provided with a cross sectional shape deviating from the circular shape, for instance, with an oval or elliptical cross sectional shape as is indicated in FIG. 3 by a dot-and-dash line at 40. It would, of course, also be possible to provide a comparatively smaller syringe body width instead of the larger width indicated, the main axis of the ellipse of the cross section of the syringe body, e.g. 3, then extending in the thickness direction of the syringe unit 14 (not illustrated).

In FIGS. 9, 9A and 9B, the mechanical filling of syringe units 14 in a filling station under sterile conditions and by preventing mutual contamination of the syringe bodies 2, 3 is schematically illustrated. In detail, in FIG. 9 four syringe units 14 each are represented in top views in two areas, wherein at first (cf. FIG. 9, left-hand area or FIG. 9A) the syringe bodies 2 are filled with a first component while covering the other syringe bodies 3 with a U-shaped angled protection means 41, in particular, a U-shaped protection plate inserted in the respective reception recesses 16. After this, cf. FIG. 9 right-hand area or FIG. 9B, the syringe units 14 are filled with the second component, wherein the first syringe bodies 2 that have already been filled are covered by an angular protection means 42 while filling the second component into the other syringe bodies 3 not covered any longer. For filling the syringe bodies 2, 3, nozzles 43, 44, which are illustrated in FIGS. 9A and 9B only very schematically, may be provided.

In order to render feasible filling of the syringe unit 1 and, subsequently, storing of the filled syringe unit 1, the syringe coni 4, 5 are closed by a closure cap 45, cf. FIGS. 9A, 9B and 10, where such closure cap 45 is shown in a sectional view.

In FIG. 9 the conveying direction of the syringe units 14 is indicated by an arrow 46. It should be noted that filling of the syringe bodies 2 of a first group of syringe units 14 while covering the syringe bodies 3 by the cover element 41, on the one hand, and of the syringe bodies 3 of a second group of syringe units 14 while covering the syringe bodies 2 by the protection means 42, on the other hand, may be effected simultaneously; to this end, the filling station may be equipped with a conveying means, such as an intermittently driven chain conveyor or the like, as is conventional per se, and this conveying means, which is not illustrated in FIG. 9, may be advanced intermittently, for instance, by a distance corresponding to four syringe units 14 each, in order to accomplish consecutive filling with the two components by preventing mutual contamination. The protection means 41, 42, in principle, may be stationarily arranged at the filling station, yet it is also possible to move or pivot them vertically to the filling station immediately before each filling procedure.

In FIG. 10, the sterile sealing of the previously filled syringe unit 14 by automatically inserting the piston plugs 28, 29 is schematically illustrated. The piston plugs 28, 29 are introduced into the syringe bodies 2, 3 from above by means of any mechanically moved plungers conventional per se.

The syringe unit 14 thus filled and closed then may be sterilely packed and conveyed off without interruption of the line including filling and closing.

FIG. 11 is a top view on the syringe unit 14 filled and closed according to FIG. 10. It is also apparent that, with this syringe unit 14, which essentially corresponds to the embodiment according to FIGS. 1 to 4, a cross strut 47 molded in one piece with the connection webs 10, 11 may be provided between the same, serving to additionally reinforce and strengthen the syringe unit 14.

From FIGS. 12 and 13 another embodiment of the piston rod unit 21' is apparent, which is particularly preferred at present, said piston rod unit 21' being intended to cooperate with the piston plugs 28', 29' consisting of full material and shown in FIG. 14.

In detail, the piston rod unit 21', similar to that according to FIGS. 1 and 3, comprises two, for instance, fully cylindrical piston rods 22, 23 having a thickness of some millimeters, which, on their upper external end, again, are interconnected in one piece by a common grip element 24'.

Figure 8:
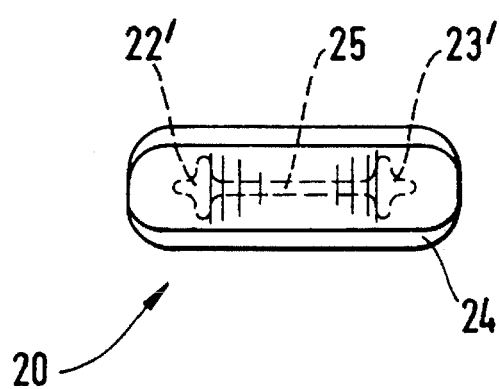
FIG. 8 is a top view on this piston rod unit.

A difference of the piston rod unit 21' according to FIGS. 12 and 13 as compared, for instance, to that according to FIGS. 7 and 8, resides in that the forward front faces of the piston rods 22, 23 terminate in a simply plane manner, having no connection means for a latch connection or the like to the piston plugs 28', 29' according to FIG. 14. Instead, it is provided with the embodiment according to FIGS. 12 to 14 that, when putting in use the filled syringe device 1 closed by the piston plugs 28', 29' according to FIG. 14, as the piston rod unit 21' according to FIGS. 12 and 13 is introduced on the rear end of the syringe unit 14, the piston rods 22, 23 simply come to abut on the external rear side of the piston plugs 28', 29'. In this manner it is achieved that the piston plugs 28', 29' can be moved only in the advancing direction for pressing the components of the biological multi-component material out of the syringe unit 14, i.e., in the direction towards the syringe coni 4, 5 (cf. FIG. 1), but not back (when retracting the piston rod unit 21', the piston rods 22, 23 move away from the piston plugs 28', 29'). Thus, it may be prevented in the most simple manner that, when using the syringe device 1, the piston plugs 28', 29' are retracted unintentionally, whereby already applied tissue adhesive would be sucked into the arrangement, thus possibly obstructing the arrangement.

Basically, this effect could be reached with the configuration according to FIGS. 7 and 8 also by rendering the latch-in or snap-in connection 30, 31 shown there such easy-going that the piston plugs 28, 29 will have a firmer interference fit within the syringe bodies 2, 3 than the latch heads 31 within the bores 30; thereby, the latch heads 31 would detach from the piston plugs 28, 29 when retracting the piston rod unit 21, thus likewise preventing the piston plugs 28, 29 from being retracted and limiting the movement of the piston plugs 28, 29 to a mere advance movement.

The configuration according to FIGS. 12 to 14, furthermore, is preferred to that according to FIGS. 7 and 8, because, when inserting the piston rod unit 21', no force need be exerted on the piston plugs 28', 29' which might result in an undesired displacement of the latter in the direction towards the syringe coni 4, 5—which, at that point of time, are still closed by the closure cap 45—or in a pressure increase within the syringe bodies 2, 3. Consequently, component material would be pressed out at the syringe coni when removing the closure cap 45, which, of course, were not desired and could be prevented only by previous retraction of the piston plugs. On the other hand, a screw connection that does not involve pressure increase, of the piston rods with the piston plugs already inserted in the syringe bodies would apparently be impossible with the instant actuation means 20 because of the one-piece design of the piston rod unit.

In order to prevent the piston rod unit 21' from undesiredly falling out of the respective syringe unit 14 with the design of the piston rod unit 21' according to FIGS. 12 and 13 (the piston rods 22, 23 may, for instance, be displaceable within the syringe bodies 2, 3 with a play of about 0.5 mm), wings or the like projections are molded to the piston rods 22, 23 in the region of their forward ends, as is indicated by 48 in FIGS. 12 and 13. These wings 48 cause the piston rod unit 21' to be slightly interference-fitted or friction-fitted within the syringe bodies 2, 3 when being inserted in the respective syringe unit 14 such that the piston rod unit 21' is held sufficiently fast within the syringe unit 14.

The piston plugs 28', 29' preferably are made of silicone caoutchouc material in order to ensure adequate sliding properties without special lubricant and even after long storage times (e.g., 1 to 2 years). Furthermore, this silicone material is beneficial if the syringe unit is filled with a tissue adhesive usually subjected to lyophilizing, because thereby the silicone material will not be affected in respect of its sliding properties.

For the sake of completeness, FIG. 15 depicts an example of the third assembly part of the whole syringe assembly, i.e., in addition to the syringe unit 14 and the piston rod unit 21 and 21', respectively, a dispensing element 50 in the form of a connection piece 51 to be slipped on the syringe coni 4, 5 of the syringe bodies 2, 3 of a syringe unit 14 (which is only partially illustrated in FIG. 15), which connection piece, in a manner known per se, carries a mixing cannula 52 and is provided with separate conveying channels or bores 53, 54 for the different components of the biological multi-component material contained in the syringe bodies 2, 3. Such a mixing cannula dispensing element is known, for instance, from EP-A-37,393, EP-A-156,098 or EP-A-210,160; an alternative dispensing element would be, for instance, the spraying head known from EP-A-37,393 or the slip-on part including a closed catheter known from EP-A-156,098.

In practice, such a dispensing element 50 may be packed in a common package together with the piston rod unit 21, 21', and the syringe unit 14 filled and closed by the piston plugs 28, 29 and 28', 29', respectively, (cf. FIGS. 10 and 11) is packed and delivered separately. However, it would, of course, also be possible to provide all three assembly parts of the described syringe assembly, i.e., the filled syringe unit closed by the piston plug as well as the piston rod unit and the dispensing element, in separate packages in a sterile manner.

Although the invention has been explained in detail by way of particularly preferred exemplary embodiments, further variations and modifications are, of course, possible within the scope of the invention. Thus, syringe units, for instance, including three parallel syringe bodies adjacently arranged in a plane are conceivable, which are interconnected to a firm syringe unit by means of connection webs as described above. Furthermore, the connection webs described, e.g., 10, 11, may be molded with reinforcement ribs like the reinforcement web 25 of the piston rod unit 21.

When filling the syringe bodies 2, 3, it is, of course, also possible to provide a simple plane vertical protection sheet instead of the inverted U-shaped protection means 41, 42, which protection sheet extends to the level of the respective nozzle 43, 44 and, by its lower end, projects into the respective reception recess (16 in FIGS. 1 and 5) of the syringe unit 14 in order to prevent mutual contamination by the respective other component.

What we claim is:

1. A syringe assembly for storing and applying a biological multi-component material, comprising as separate assembly components:

(a) a syringe device including at least two parallel syringe bodies ending in coni and each filled with one of said multi-component material, a connection part connecting said syringe bodies, and piston plugs closing said syringe bodies in the filled state;

(b) an actuation means including piston rods associated with said piston plugs and a common grip element; and (c) a dispensing element capable of being attached to said coni of said syringe bodies; wherein said syringe bodies, after having been filled and separately closed by said piston plugs, constitute a one-piece syringe unit with said connection part, said connection part, on one end of said syringe unit, leaves a recess between said syringe bodies, and said grip element is connected in one piece with said piston rods, thus forming a one-piece piston rod unit separate from said syringe unit including said piston plugs.

2. A syringe assembly as set forth in claim 1, wherein said syringe unit has an end opposite said coni and said recess is provided on said end opposite said coni.

3. A syringe assembly as set forth in claim 1, wherein said syringe unit comprises X-ray-tight material at least in regions thereof.

4. A syringe assembly as set forth in claim 3, wherein said X-ray-tight material is in the form of a strip.

5. A syringe assembly as set forth in claim 1, wherein said piston rod unit comprises X-ray-tight material at least in regions thereof.

6. A syringe assembly as set forth in claim 5, wherein said X-ray-tight material is in the form of a strip.

7. A syringe assembly as set forth in claim 1, wherein said dispensing element comprises X-ray-tight material at least in regions thereof.

8. A syringe assembly as set forth in claim 7, wherein said X-ray-tight material is in the form of a strip.

9. A syringe assembly as set forth in claim 1, wherein said piston plugs are arranged for displacement within said syringe bodies by said piston rod unit only in the direction of said coni.

10. A syringe assembly as set forth in claim 1, wherein said piston plugs are made of silicone material.

11. A syringe device for storing and applying a biological multi-component material, comprising at least two parallel syringe bodies made of a synthetic material, ending in coni and each filled with one of said multi-component material, at least one connection part adapted to connect said syringe bodies and constituting a one-piece syringe unit with said syringe bodies, and piston plugs adapted to close said syringe bodies, wherein said connection part, on one end of said syringe unit, leaves a recess between said syringe bodies.

12. A syringe device as set forth in claim 11, wherein said syringe unit has an end opposite said coni and said recess is provided on said end opposite said coni.

13. A syringe device as set forth in claim 11, wherein said connection part is comprised of at least two parallel plate-shaped connection webs extending between said syringe bodies thereby interconnecting said syringe bodies to one piece.

14. A syringe device as set forth in claim 13, wherein each of said at least two connection webs tangentially joins the respective one of said syringe bodies.

15. A syringe device as set forth in claim 11, wherein each of said syringe bodies has a syringe body external diameter and said syringe unit is flat and plate-shaped, having a thickness corresponding to said syringe body external diameter.

16. A syringe device as set forth in claim 15, wherein said syringe bodies have different cross sectional areas and constant piston stroke lengths, the cross sectional area of at least one of said syringe bodies being oval and its dimension transverse to the thickness direction of said plate-shaped syringe unit being different from that of the cross sectional area of the other of said syringe bodies.

17. A syringe device as set forth in claim 11, wherein said syringe bodies have longitudinal axes defining a median plane and said connection part is comprised of at least one connection web extending in a plate-shaped manner in accordance with said median plane and following centrally on the respective one of said syringe bodies.

18. A syringe device as set forth in claim 11, wherein the respective connection part terminates at a distance of at least 2 mm from one end of said syringe unit so as to leave said reception recess.

19. A syringe device as set forth in claim 18, wherein the respective connection part terminates at a distance of between 5 mm and 15 mm from one end of said syringe unit.

20. A syringe device as set forth in claim 18, wherein the respective connection part terminates at a distance of about 10 mm from one end of said syringe unit.

21. A syringe device as set forth in claim 11, further comprising finger grips laterally projecting from said syringe bodies and wherein said finger grips are molded directly to said syringe bodies to their rear ends.

22. A syringe device as set forth in claim 11, wherein said syringe unit is a one-piece polypropylene injection-molded part.

23. A syringe device as set forth in claim 11, wherein said at least one connection part comprises at least one inscription area.

24. A syringe device as set forth in claim 11, wherein said syringe unit comprises X-ray-tight material, at least in regions thereof.

25. A syringe device as set forth in claim 24, wherein said X-ray-tight material is in the form of a strip.

26. A syringe device as set forth in claim 11, wherein separate piston plugs are inserted in said syringe bodies after filling thereof for closing said syringe bodies.

27. A syringe device as set forth in claim 26, wherein said piston plugs are arranged for displacement only in the direction of said coni.

28. A syringe assembly as set forth in claim 26, wherein said piston plugs are made of silicone material.

29. A syringe assembly as set forth in claim 1, wherein said actuation means further comprises a reinforcement web following on said grip element and extending between said piston rods, said reinforcement web being firmly connected with said piston rods.

30. A syringe assembly as set forth in claim 1, wherein said piston rod unit is a one-piece injection-molded part.

31. A syringe assembly as set forth in claim 1, wherein said piston rod unit is comprised of an acrylonitrile-butadiene-styrene copolymer.

32. A syringe assembly as set forth in claim 1, wherein said connection part, or one end of said syringe unit, leaves a recess between said syringe bodies suited to temporarily receive a protection means therein to shield off the other of said at least two syringe bodies during filling of a respective one of said syringe bodies.

33. A syringe assembly as set forth in claim 11, wherein said connection part, or one end of said syringe unit, leaves a recess between said syringe bodies suited to temporarily receive a protection means therein to shield off the other of said at least two syringe bodies during filling of a respective one of said syringe bodies.

34. A method of producing a filled sterile syringe device including at least two parallel syringe bodies filled with a biological multi-component material, a connection part adapted to connect said syringe bodies and constituting a syringe unit therewith, and piston plugs adapted to close said syringe bodies, said connection part leaving a recess between said syringe bodies on one end of said syringe unit, which method comprises the steps of providing a sterile one-piece syringe unit, sealing each of said syringe bodies on one of its ends, introducing a protection means into said recess for for shielding off the respective other of said at least two syringe bodies, automatically filling each component of said biological multi-component material in the respective one of said syringe bodies on its other end in a filling station and under sterile conditions, and closing said syringe bodies with said piston plugs being sterile.

35. A method as set forth in claim 34, wherein said syringe unit is sterilely produced and kept sterile.

36. A method as set forth in claim 34, wherein said syringe unit is sterilized after production.

37. A method as set forth in claim 34, further comprising sterilely packing said syringe device immediately upon filling with said components and closing by said piston plugs.

38. A method as set forth in claim 34, wherein several syringe units are arranged in a row and the corresponding ones of said syringe bodies are sterilely filled simultaneously while introducing respective common protection means into recesses provided between said syringe units.

* * * * *